(12) United States Patent
Nye et al.

(10) Patent No.: US 10,702,217 B2
(45) Date of Patent: Jul. 7, 2020

(54) SYSTEM AND METHOD FOR IMAGING A PATIENT

(71) Applicant: GENERAL ELECTRIC COMPANY, Schenectady, NY (US)

(72) Inventors: Katelyn Rose Nye, Glendale, WI (US); Benjamin James Beeman, Leland, NC (US); Tabb Patz, New Berlin, WI (US); Gireesha Rao, Pewaukee, WI (US); Cheryl Ruth Jones, Hubertus, WI (US); Kristine Gould, Delafield, WI (US); Robert Buchanan, Dousman, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 245 days.

(21) Appl. No.: 15/685,310

(22) Filed: Aug. 24, 2017

(65) Prior Publication Data

US 2019/0059828 A1 Feb. 28, 2019

(51) Int. Cl.

| A61B 6/02 | (2006.01) |
|---|---|
| G01N 23/04 | (2018.01) |
| A61B 6/00 | (2006.01) |
| G01N 23/044 | (2018.01) |
| A61B 6/12 | (2006.01) |

(52) U.S. Cl.
CPC ............ *A61B 6/025* (2013.01); *A61B 6/4464* (2013.01); *A61B 6/5223* (2013.01); *G01N 23/04* (2013.01); *G01N 23/044* (2018.02); *A61B 6/12* (2013.01); *A61B 6/488* (2013.01); *A61B 6/502* (2013.01); *A61B 6/547* (2013.01); *G01N 2223/419* (2013.01)

(58) Field of Classification Search
CPC ......... A61B 6/025; A61B 6/12; A61B 6/4464; A61B 6/488; A61B 6/502; A61B 6/5223; A61B 6/547; G01N 2223/419; G01N 23/04
See application file for complete search history.

(56) References Cited

U.S. PATENT DOCUMENTS

| 4,674,046 A * | 6/1987 | Ozeki ................. A61B 6/4447 324/312 |
|---|---|---|
| 5,872,828 A | 2/1999 | Niklason et al. |
| 8,774,355 B2 | 7/2014 | Claus et al. |

(Continued)

FOREIGN PATENT DOCUMENTS

EP 1428473 A2 6/2004

*Primary Examiner* — Marcus H Taningco
(74) *Attorney, Agent, or Firm* — Grogan, Tuccillo & Vanderleeden, LLP (57) ABSTRACT

A system for imaging a subject is provided. The system includes a radiation source, a radiation detector, and a controller. The radiation source is operative to transmit electromagnetic rays through the subject. The radiation detector is operative to receive the electromagnetic rays after having passed through the subject so as to generate a plurality of projections of the subject. The controller is operative to display one or more selectively adjustable markers that define an image stack. The controller is further operative to reconstruct one or more images within the image stack based at least in part on the plurality of projections. Reconstruction of the one or more images is on demand.

20 Claims, 11 Drawing Sheets

(56) References Cited

U.S. PATENT DOCUMENTS

| | | | | |
|---|---|---|---|---|
| 2004/0199066 A1* | 10/2004 | Kawachi | ............... | G06F 19/321 600/407 |
| 2011/0102430 A1* | 5/2011 | Eberhard | ............. | G06T 11/008 345/420 |
| 2013/0257869 A1* | 10/2013 | Lao | ......................... | G06T 15/08 345/424 |
| 2015/0049934 A1* | 2/2015 | Ruth | .................... | G06K 9/4638 382/131 |
| 2015/0052471 A1* | 2/2015 | Chen | ...................... | A61B 6/025 715/771 |
| 2016/0345925 A1* | 12/2016 | Westerhoff | ........... | A61B 6/5223 |
| 2017/0281110 A1* | 10/2017 | Mandelkern | ........... | A61B 6/025 |

\* cited by examiner

SYSTEM AND METHOD FOR IMAGING A PATIENT

BACKGROUND

Technical Field

Embodiments of the invention relate generally to medical technologies, and more specifically, to a system and method for imaging a patient.

Discussion of Art

Digital tomosynthesis is an imaging technology that provides for volume data acquisition from selected regions of a body. Many tomosynthesis systems include a mobile arm that moves a radiation source along a curved and/or linear path with respect to a subject such that a plurality of projections of a body part are obtained. A digital processor then reconstructs a three dimensional ("3D") image/model of the subject from the projections. Unlike traditional computed tomography ("CT"), which involves the reconstruction of a 3D image from projections that form a complete circumference around a subject, the projections utilized in tomosynthesis typically form a partial circumference, i.e., an arc, as opposed to a full circle. Moreover, many tomosynthesis systems only move/sweep the radiation source along the path once during a scan. Accordingly, the acquisition parameters of many tomosynthesis systems must be tightly controlled during a scanning procedure in order to mitigate the risk of artifacts and/or other imaging errors.

In many tomosynthesis systems, reconstruction of the images from the acquired projections is a time consuming process that depends on numerous parameters. Moreover, many tomosynthesis systems may not provide for an operator to view the reconstructed images until all of the images of a requested stack have been processed. Thus, operators of such tomosynthesis systems must often wait for reconstruction of a full image stack prior to verifying that the images in the stack are acceptable, e.g., conducive for medical diagnosis, and to adjust the parameters if needed. Adjustment of the parameters, however, usually requires the entire image stack to be reconstructed again. While some traditional tomosynthesis systems provide initial default parameters, such systems may fail to provide any real-time and/or dynamic guidance to operators for adjusting/tuning the parameters to a particular subject and acquisition type prior to reconstruction of an entire image stack.

What is needed, therefore, is an improved system and method for imaging a subject.

BRIEF DESCRIPTION

In an embodiment, a system for imaging a subject is provided. The system includes a radiation source, a radiation detector, and a controller. The radiation source is operative to transmit electromagnetic rays through the subject. The radiation detector is operative to receive the electromagnetic rays after having passed through the subject so as to generate a plurality of projections of the subject. The controller is operative to display one or more selectively adjustable markers that define an image stack. The controller is further operative to reconstruct one or more images within the image stack based at least in part on the plurality of projections. Reconstruction of the one or more images is on demand.

In another embodiment, a method for imaging a subject is provided. The method includes displaying, via a controller, one or more selectively adjustable markers that define an image stack; and reconstructing, via the controller, one or more images within the image stack based at least in part on a plurality of projections generated by receiving, at a radiation detector, electromagnetic rays transmitted through the subject via a radiation source. Reconstruction of the one or more images is on demand.

In yet another embodiment, a non-transitory computer readable medium storing instructions is provided. The stored instructions are configured to adapt a controller to: display one or more selectively adjustable markers that define an image stack; and to reconstruct one or more images within the image stack based at least in part on a plurality of projections generated by receiving, at a radiation detector, electromagnetic rays transmitted through a subject via a radiation source. Reconstruction of the one or more images is on demand.

DRAWINGS

The present invention will be better understood from reading the following description of non-limiting embodiments, with reference to the attached drawings, wherein below.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process. As further used herein, the terms "scan," "procedure," and/or "imaging procedure" refer to the acquisition of data by an imaging system from which one or more images of a subject may be generated from. The term "imaging parameter," as used herein, means a setting of a device, or a property of a subject to be imaged, that affects the operation of an imaging system. The terms "scout image" and "pre-shot," as used herein, refer to an image of a subject acquired by an imaging system and analyzed prior to the imaging system acquiring subsequent images of the subject. The term "image look," as used herein, refers to a group of preferred reconstruction parameters for a corresponding anatomy, e.g., contrast, brightness, tissue contrast, and/or edge contrast.

Additionally, while the embodiments disclosed herein are described with respect to an x-ray based imaging system, e.g., a tomosynthesis imaging system, it is to be understood that embodiments of the present invention are equally applicable to other devices and/or imaging systems which preform tomography and/or reconstruct image stacks, i.e., a collection/grouping of one or more images. Further, embodiments of the present invention related imaging systems may be used to analyze objects within any material which can be internally imaged, generally. As such, embodiments of the present invention are not limited to analyzing objects within human tissue.

Figure 1:
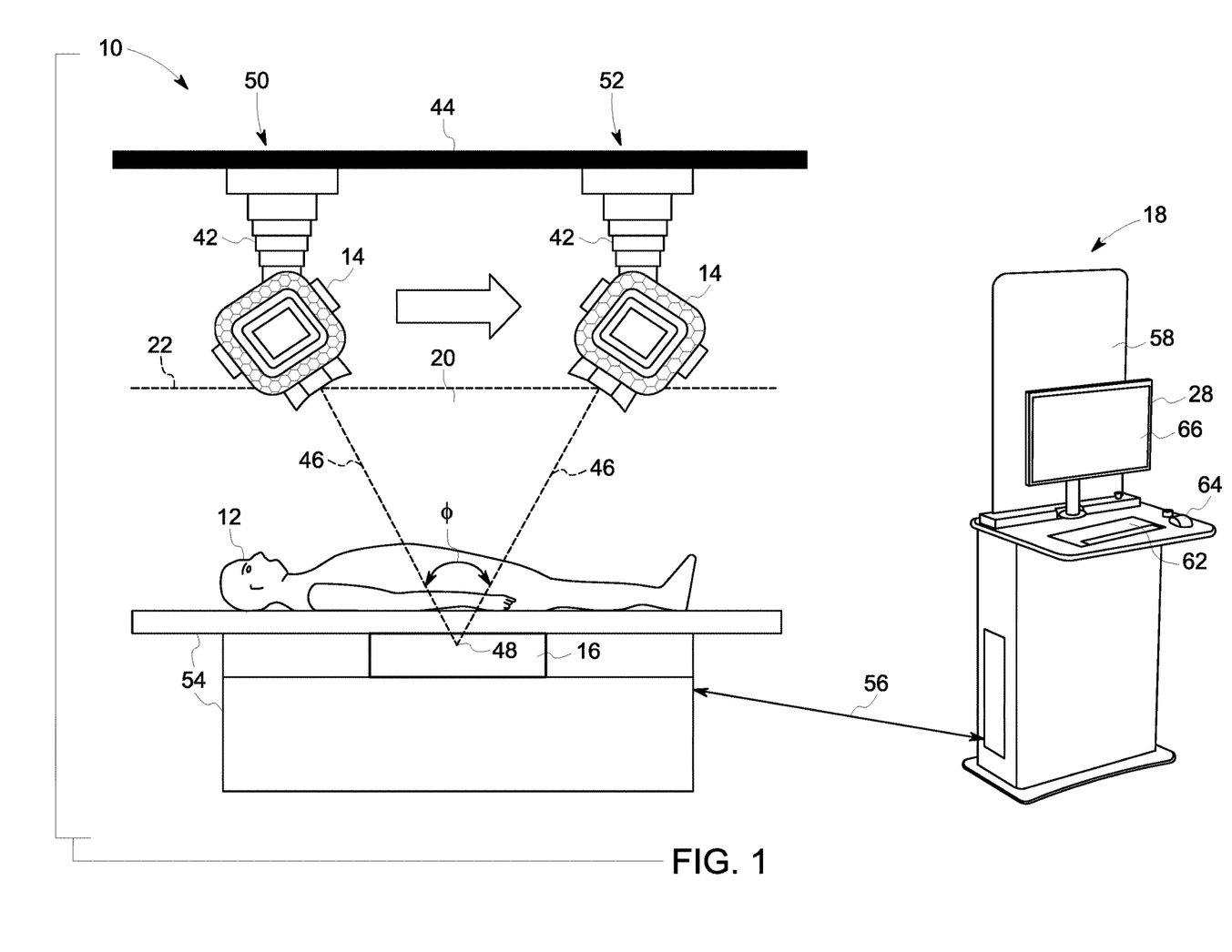
FIG. 1 is a schematic diagram of a system for imaging a subject, in accordance with an embodiment of the invention.
Figure 2:
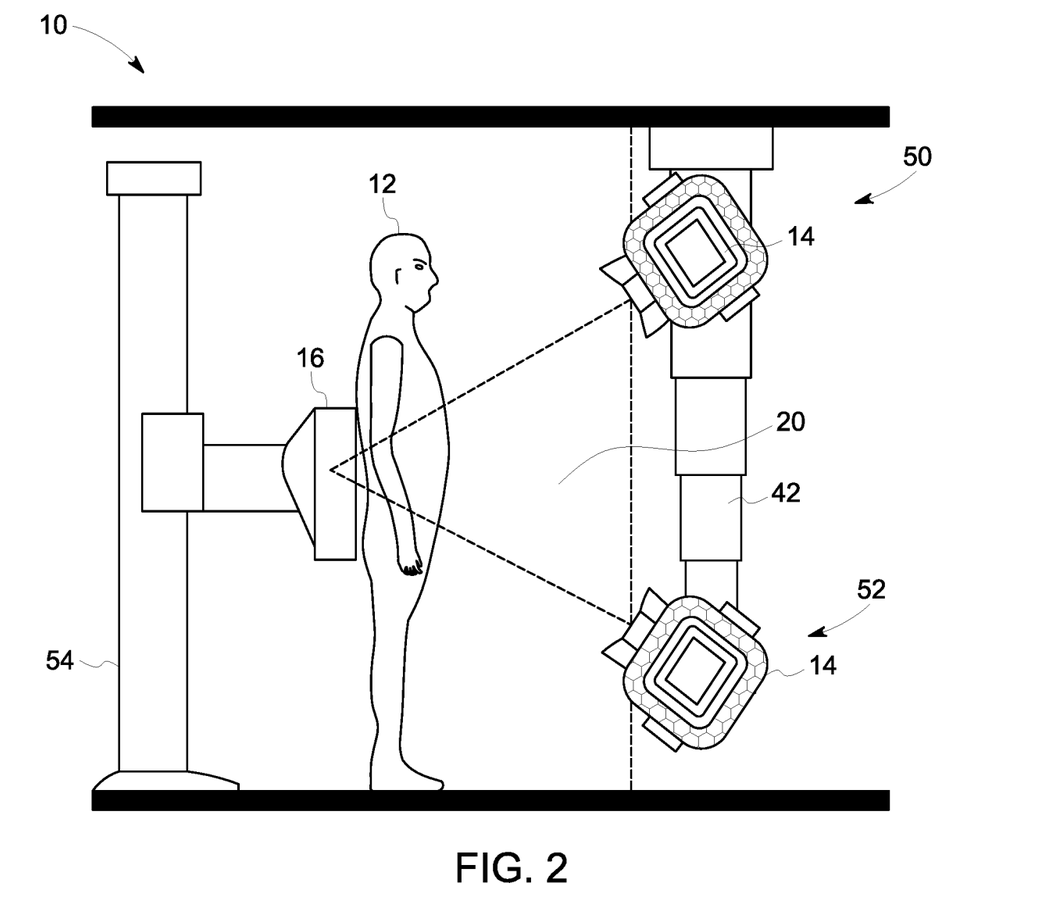
FIG. 2 is schematic diagram of another orientation of the system of FIG. 1, in accordance with an embodiment of the invention.
Figure 3:
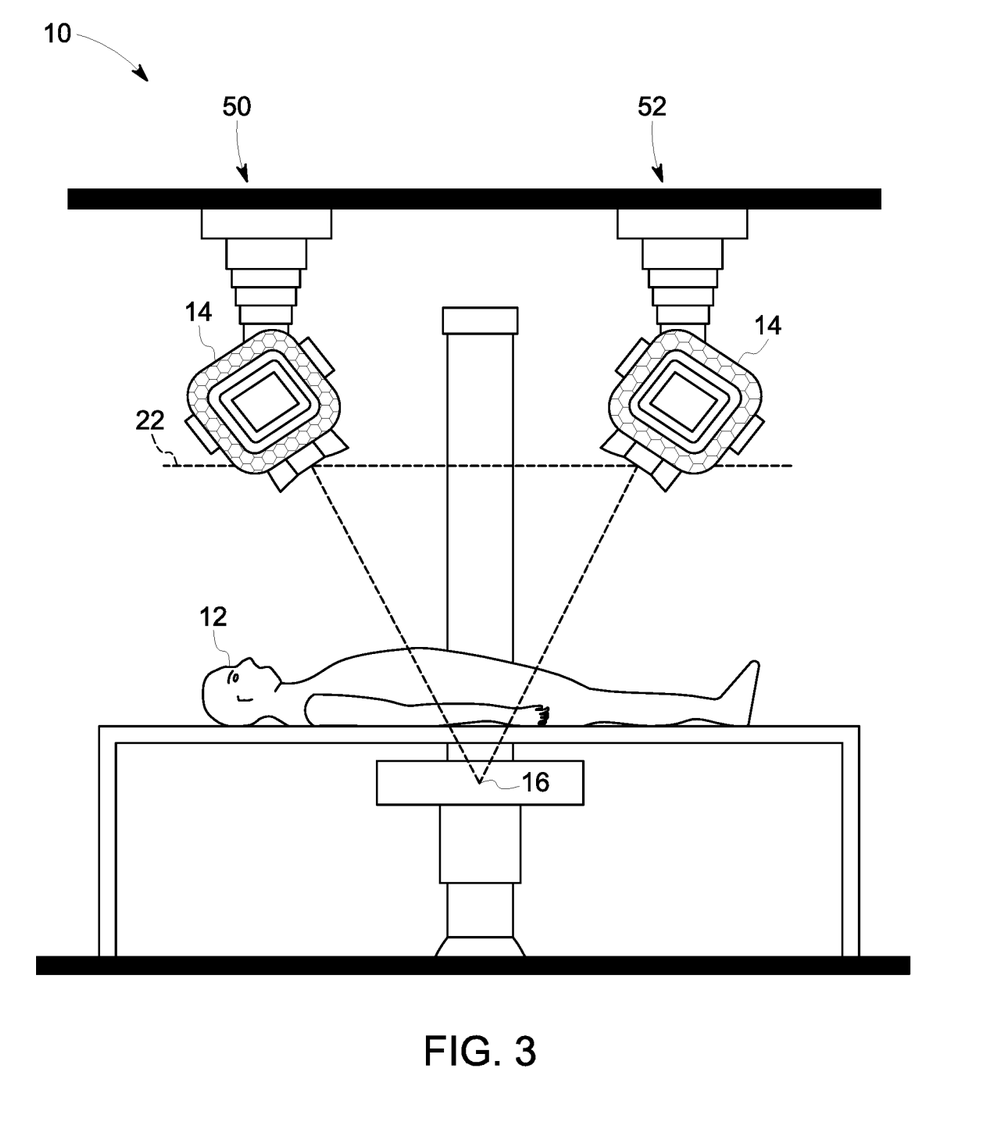
FIG. 3 is a schematic diagram of yet another orientation of the system of FIG. 1, in accordance with an embodiment of the invention.
Figure 4:
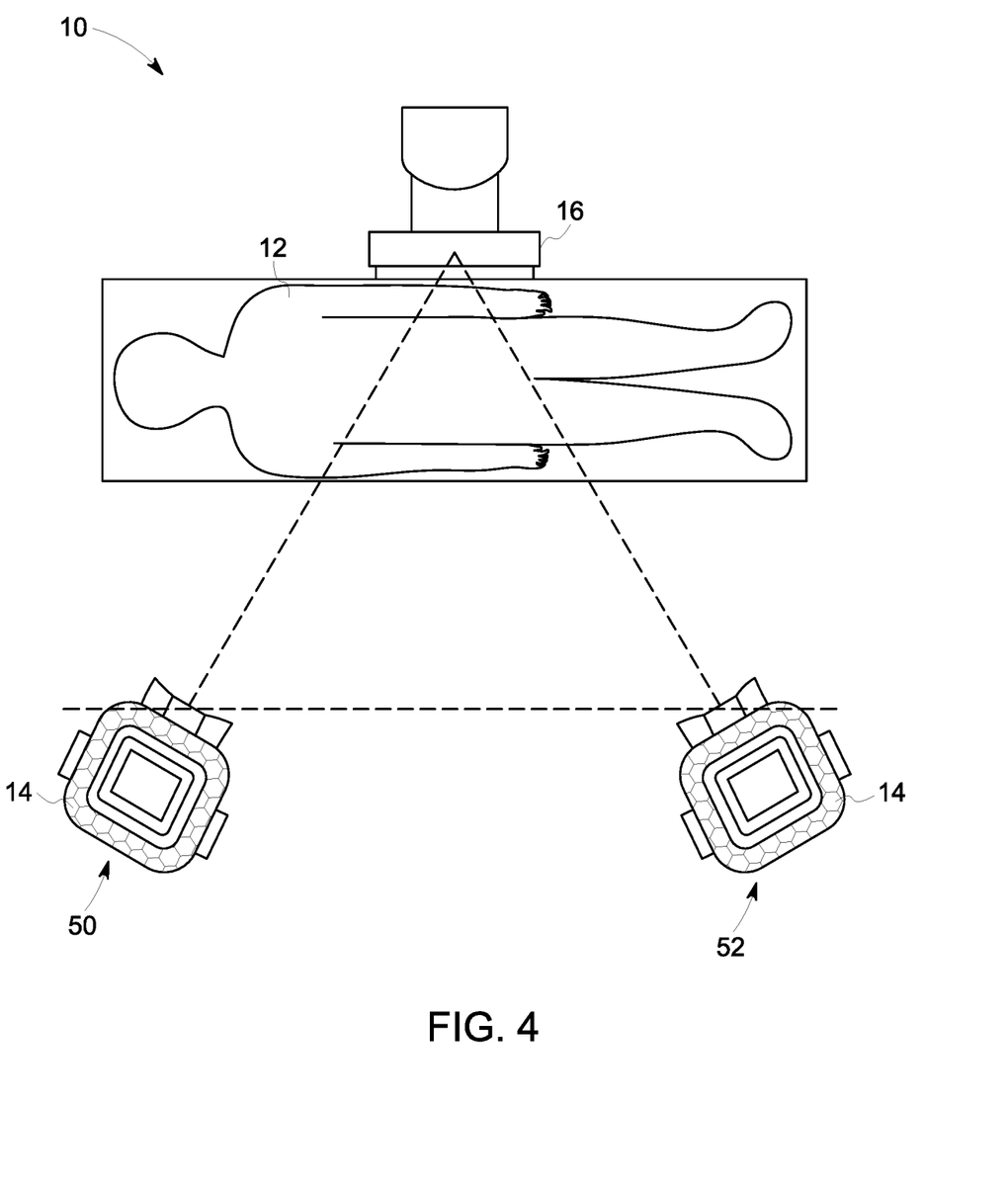
FIG. 4 is a schematic diagram of still yet another orientation of the system of FIG. 1, in accordance with an embodiment of the invention.
Figure 5:
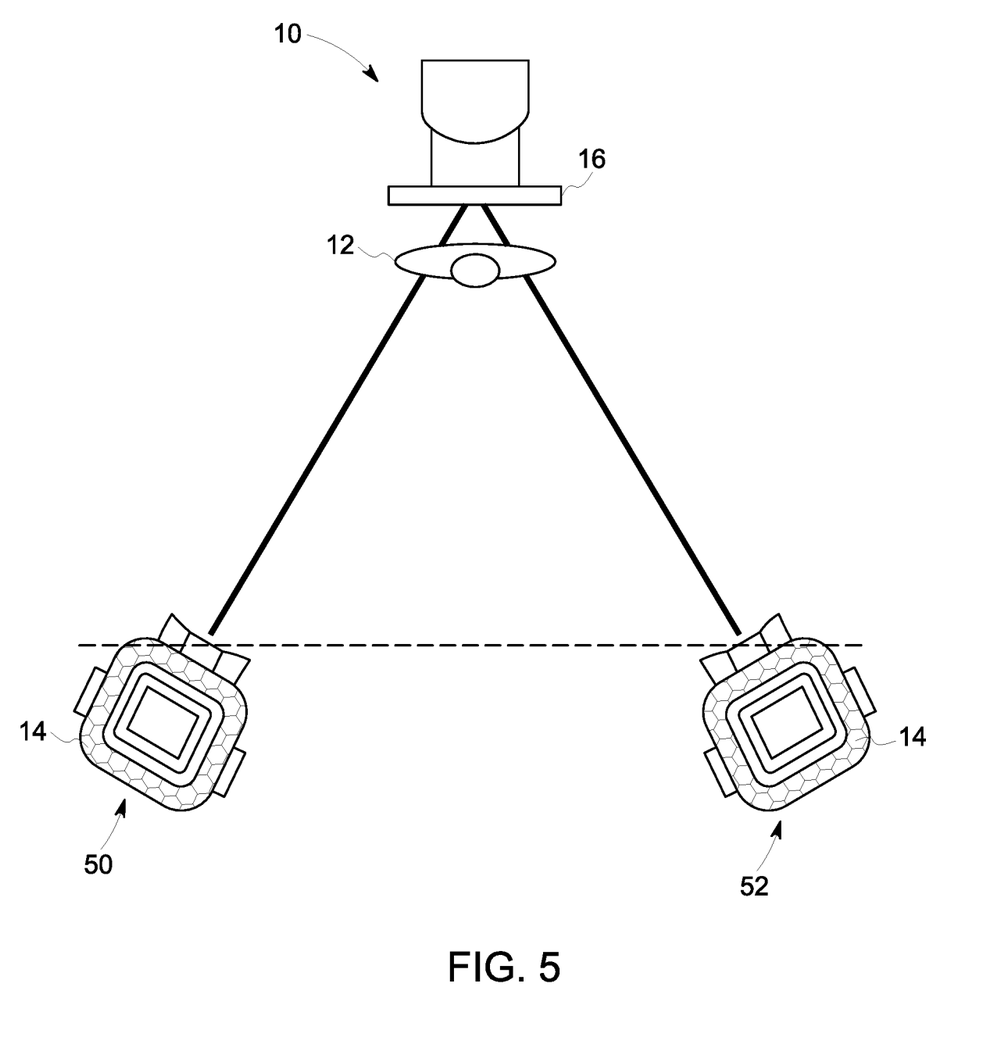
FIG. 5 is a schematic diagram of still yet another orientation of the system of FIG. 1, in accordance with an embodiment of the invention.

Referring now to FIG. 1, the major components of a system 10 for imaging a subject/object/patient 12, in accordance with an embodiment of the invention, are shown. The system 10 includes a radiation source/device 14, a radiation detector 16, and a controller 18. The radiation source 14 is operative to transmit electromagnetic rays/radiation 20 through the subject 12 while the radiation source 14 travels along a path 22 defined by a sweep angle Ø. The radiation detector 16 is operative to receive the electromagnetic rays 20 after having passed through the subject 12. The controller 18 is operative to display one or more selectively adjustable markers 24, 26 (FIGS. 8-11), which may be on a display/screen 28, that define an image stack 30 (best seen in FIG. 7) that includes a plurality of images/slices 32, 34, 36, 38, 40 (FIG. 7), and to reconstruct one or more images/slices 32, 34, 36 within the image stack 30 based on the projections. As will be appreciated, reconstruction of the images 32, 34, 36 is "on demand," which, as used herein, means that the one or more images 32, 34, 36 are reconstructed by the controller 18 separately and prior to reconstruction of the majority of the images in the stack 30. Reconstruction of the images 32, 34, 36, 38, 40, to include the on demand reconstruction of images 32, 34, and/or 36, is based on the reconstruction parameters. Thus, the one or more on demand reconstructed images 32, 34, 36 may be analyzed to determine if one or more reconstruction parameters of the system 10 need to be adjusted prior to reconstructing the majority of the images in the image stack 30. As will be understood, reconstruction may be performed via a reconstruction algorithm, e.g., filtered back projection, iterative reconstruction, metal artifact reduction, multiplanar, and/or other suitable reconstruction algorithms and/or combinations thereof.

Accordingly, as shown in FIG. 1, the radiation source 14 may be rotatably mounted to a mobile arm 42 secured to a support structure 44, e.g., a mount and/or the ceiling of a room, such that the radiation source 14 is able to train the electromagnetic rays 20 along a line of projection 46 that continuously intersects a target location 48 on the radiation detector 16 as the mobile arm 42 moves the radiation source 14 along the path 22. The path 22 may have a start 50 position and an end/stop position 52 such that the line of projection 46 sweeps an area of the subject 12 defined by the sweep angle Ø. As will be appreciated, while the path 22 is shown herein as being linear, it will be understood that, in other embodiments, the path 22 may have a curved shape and/or any other shape configured for tomosynthesis. Further, the sweep angle Ø may be less than 365°, and in some embodiments, may be between about 0° to 180°, 20° to 100°, 20° to 80°, 20° to 40°, or 20° to 30°. As will be appreciated, in some embodiments, the sweep angle Ø may be greater than or equal to 365°. Further still, While the radiation rays 20 are discussed herein as being x-rays, it is to be understood that the radiation source 14 may emit other types of electromagnetic rays, e.g., radio waves, visible light, ultra-violet light, gamma rays, etc., which can be used to image the subject 12.

Figure 6:
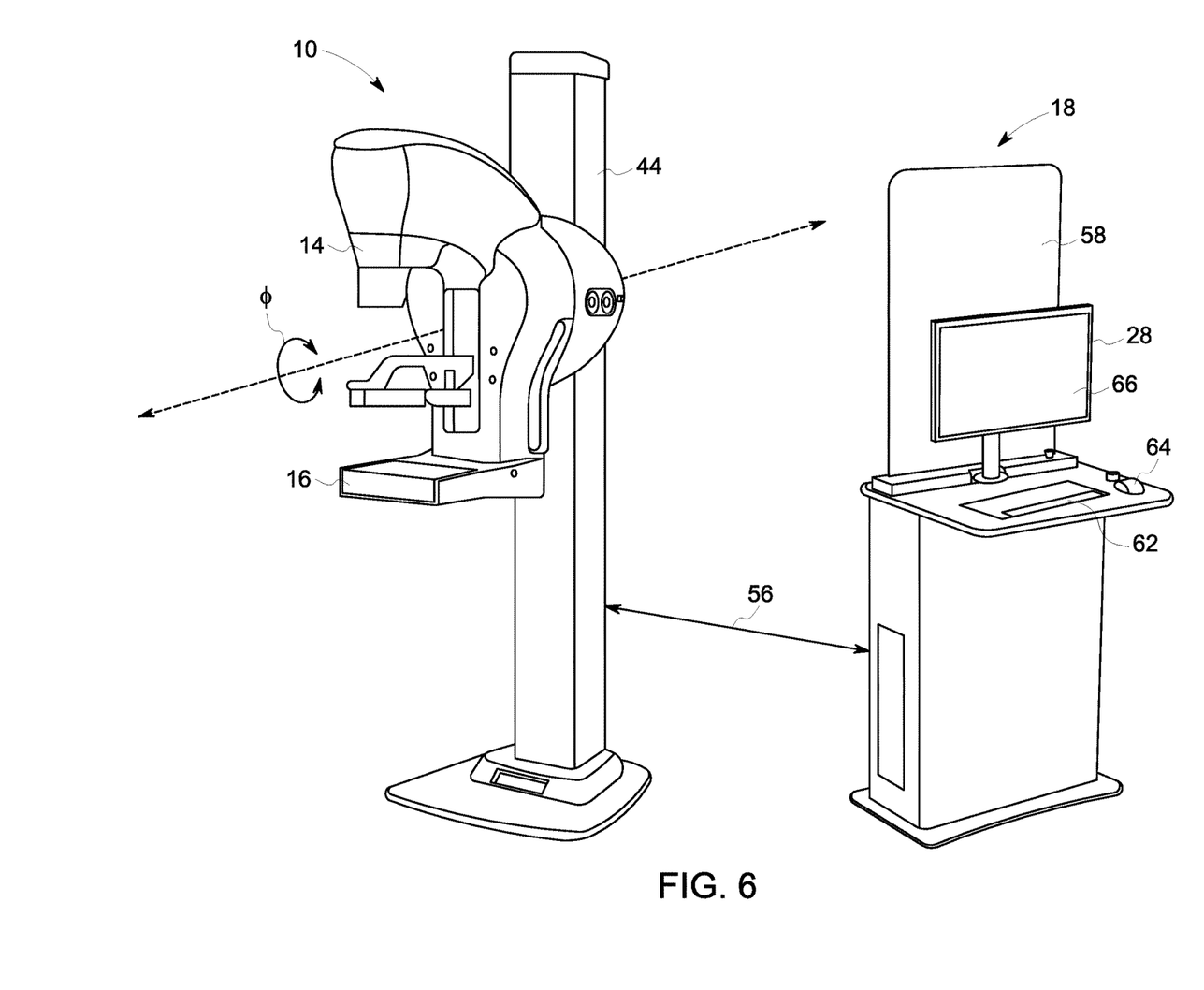
FIG. 6 is a schematic diagram of still yet another orientation of the system of FIG. 1, in accordance with an embodiment of the invention.

As further shown in FIG. 1, the radiation detector 16 is positioned opposite the radiation source 14 such that the subject 12 is disposed between the radiation source 14 and the radiation detector 16. While the radiation detector 16 is depicted herein as being stationary with respect to the subject 12, it will be understood, that, in other embodiments, the radiation detector 16 may move in relation to the subject 12. Additionally, the radiation detector 16 may be integrated into a subject support structure 54, e.g., a table and/or other platform structure which, in embodiments, may be operative to support the entire subject 12 or a part of the subject 12. For example, as shown in FIGS. 1-6, in embodiments, the system 10 may be configured to perform a table horizontal sweep (FIG. 1) for supine imaging, a wallstand vertical sweep (FIG. 2) for upright imaging, a wallstand horizontal sweep (FIG. 3) for supine imaging, a wallstand cross-table sweep for cross-table imaging of a patient laying down (FIG. 4) and/or standing (FIG. 5); and/or a mammography sweep (FIG. 6).

The controller 18 may be a workstation having at least one processor and a memory device as shown in FIG. 1 or, in other embodiments, the controller 18 may be embedded/integrated into one or more of the various components of the system 10 disclosed above. In embodiments, the controller 18 may be in electrical communication with the radiation source 14 and/or the radiation detector 16 via an electrical communication connection 56. The connection 56 may be a wired and/or wireless connection. As will be appreciated, in embodiments, the controller 18 may include a radiation shield 58 that protects an operator of the system 10 from the radiation rays 20 emitted by the radiation source 14. The controller 18 may further include the display 28, a keyboard 62, mouse 64 and/or other appropriate user input devices, that facilitate control of the system 10 via a user interface 66. Data regarding the radiation rays 20 received by the radiation detector 16 may be electrically communicated to the controller 18 from the radiation detector 16 via cable/electronic connection 56 so that the controller 18 generates/reconstructs the images 32, 34, 36, 38, 40, which, in embodiments, may be shown on/in the interface 66. As will be understood, in embodiments, the interface 66 may be accessible over a network, e.g., the Internet, via a web browser on an external workstation and/or mobile device. Thus, in some embodiments, a user of a mobile device need not be in the same room and/or building as the subject/patient 12 in order to perform image reconstruction as described herein.

Figure 7:
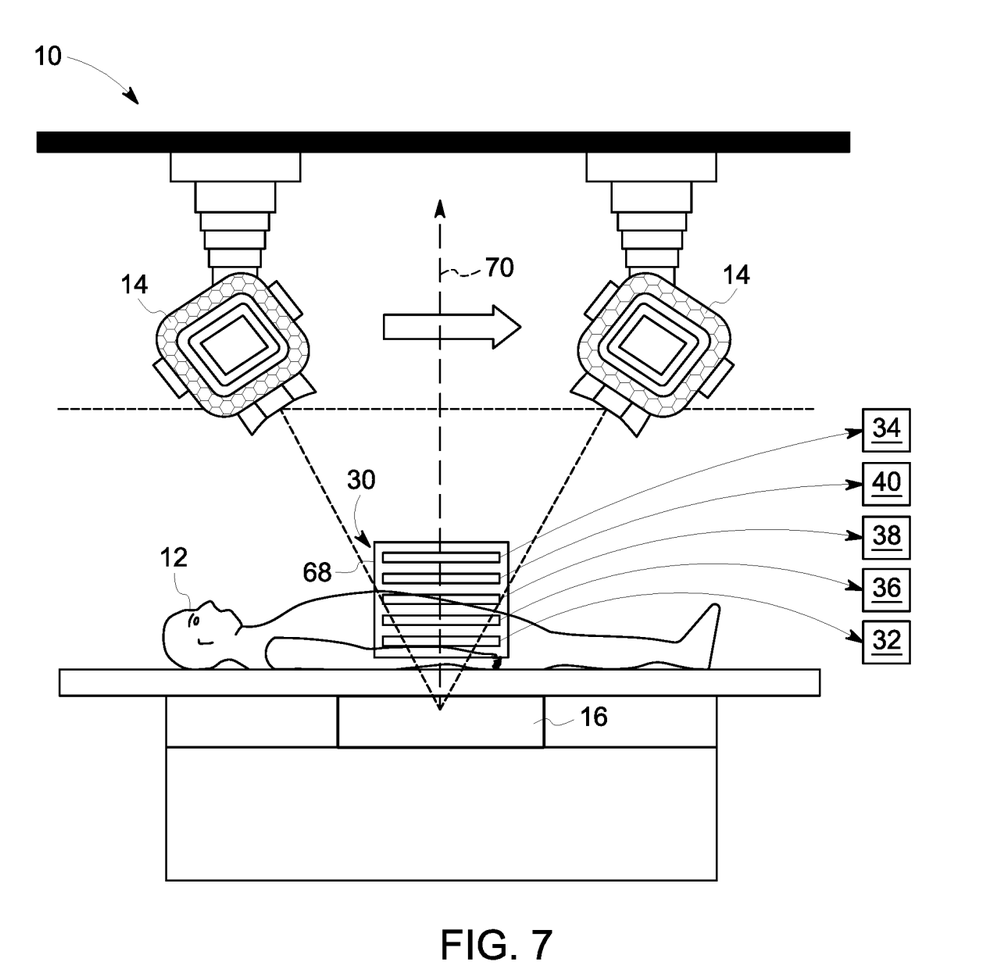
FIG. 7 is another schematic diagram of the system of FIG. 1, in accordance with an embodiment of the invention.

Turning to FIG. 7, as stated above, the image stack 30 includes a plurality of images 32, 34, 36, 38, 40 reconstructed from projections of the subject 12 acquired via the radiation source 14 and detector 16. The images 32, 34, 36, 38, 40 within the stack 30 may be oriented such that they provide a slice by slice view of the internal structure of the subject 12 within a given volume 68 along an axis 70 that extends from the radiation detector 16 and passes through the volume 68. As will be understood, distances along the axis 70, as described herein, begin at the point where the axis 70 intersects the detector 16 and extend/increase outward towards the radiation source 14. Further, the volume 68 may encompass a distance of up to and including 400 mm×400 mm×700 mm extending out from the radiation detector 16.

Figure 8:
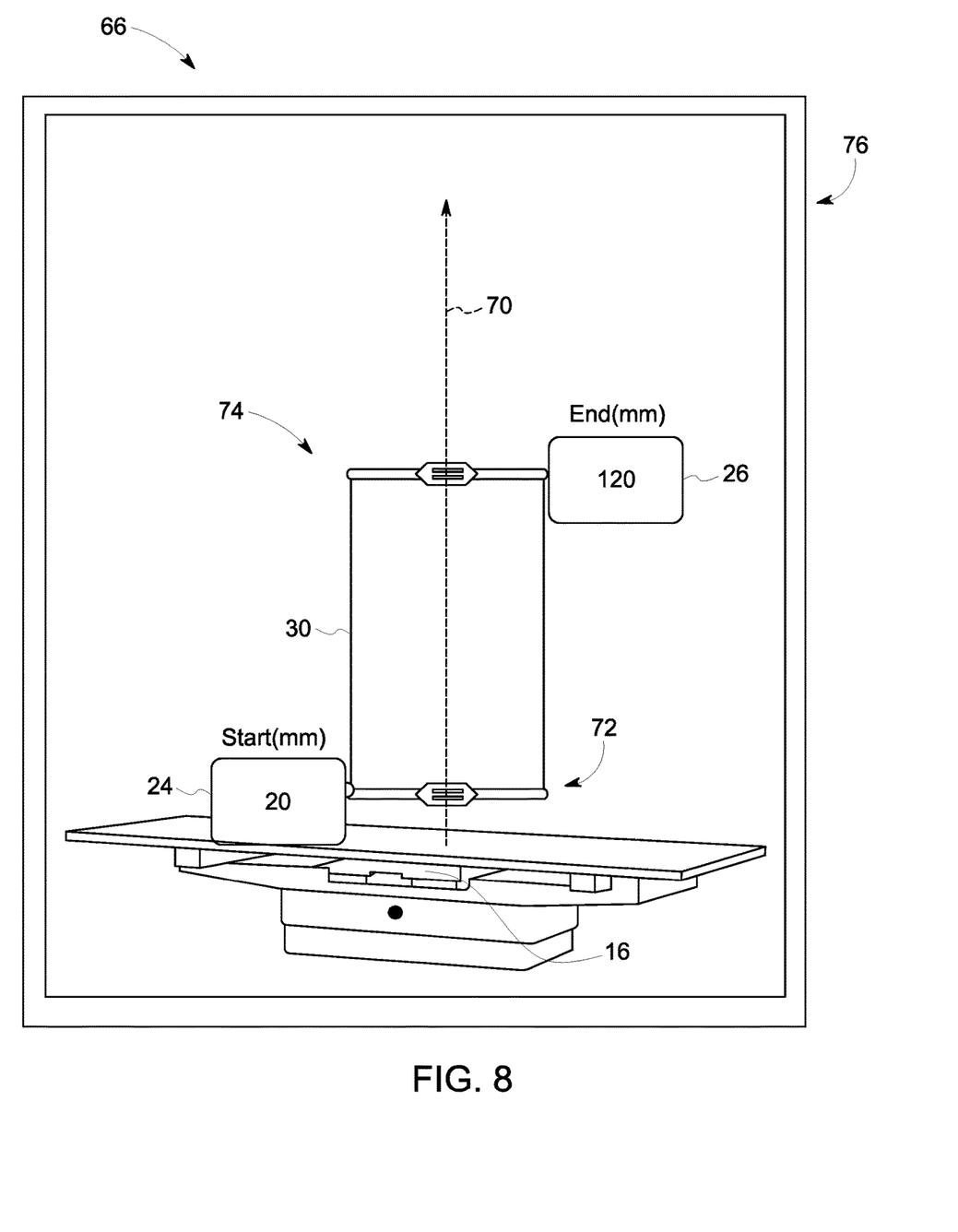
FIG. 8 is a graphical display of an interface of the system of FIG. 1, in accordance with an embodiment of the invention.
Figure 9:
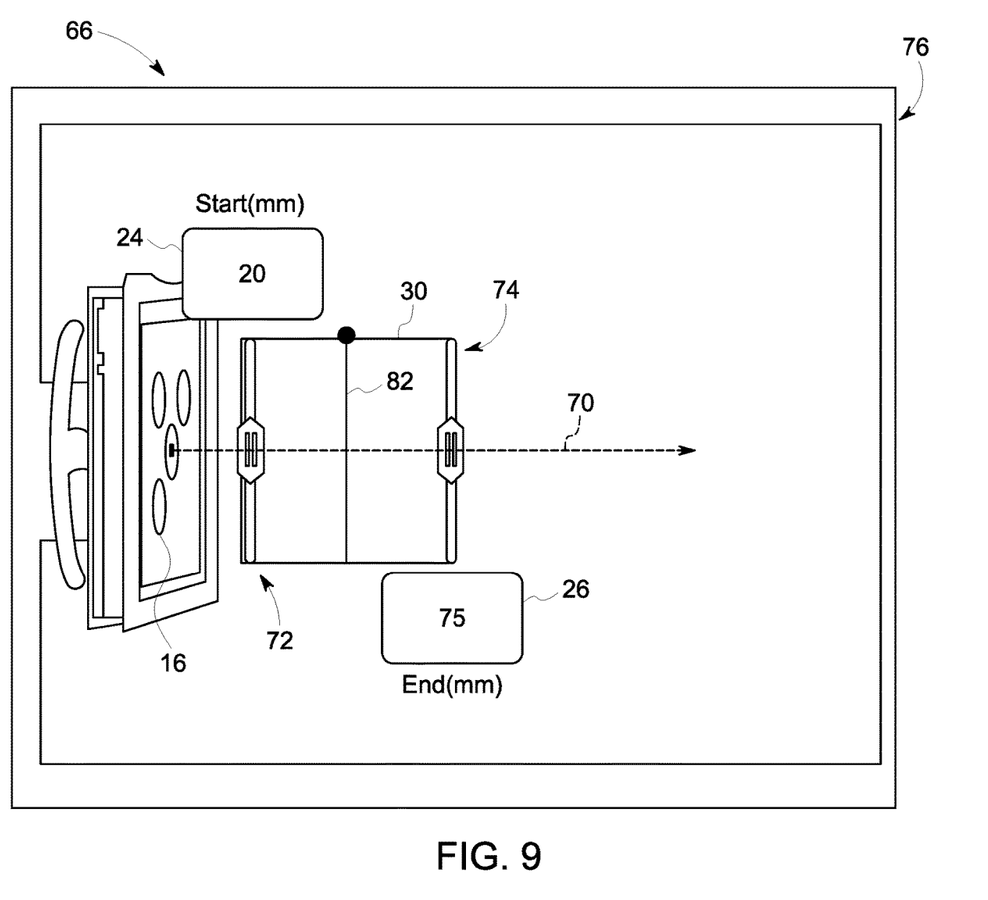
FIG. 9 is another graphical display of the interface of the system of FIG. 1, in accordance with an embodiment of the invention.

Moving to FIGS. 8 and 9, in embodiments, the markers 24, 26 may be displayed within the interface 66 on the screen 28 such that the markers 24, 26 define the image stack 30. For example, in embodiments, the markers 24, 26 may correspond to a distance/location/position along the axis 70, e.g., 20 mm and 120 mm as shown in FIG. 8. Accordingly, in embodiments, a first marker 24 of the one or more markers and a second marker 26 of the one or more markers may correspond to a first/start/initial/bottom position 72 of the image stack 30 and a second/stop/end/top position 74 of the image stack 30, respectively; the image stack 30 including additional slices/images disposed between the top 74 and bottom 72 positions and perpendicular to the axis 70, i.e., the axis 70 is normal to the slices/images. In embodiments, the image stack 30 may be similarly defined in relation to a single marker 24, e.g., the image stack 30 may include a given number of slices/images above and/or below an individual marker 24 and perpendicular to the axis 70.

Further, in embodiments, the interface 66 may not display the entire range of the stack 30, e.g., the distance from the bottom 72 to the top 74 position. For example, the interface 66 may only display thirty percent (30%) of the stack 30 above and/or below a position, defined by a marker 24, 26, along the axis 70 so that an operator of the system 10 may more easily make minor/small/fine adjustments to one or more of the markers 24, 26. In such embodiments, if an operator adjusts a marker 24, 26 to be at limit of the shown range, the controller 18 may automatically readjust/refresh the interface 66 such that the scale of the axis 70 is adjusted so that an additional, e.g., thirty percent (30%), of the stack 30 is shown within the interface 66. For example, in a scenario where the system 10 is capable of imaging a volume 68 (FIG. 7) encompassing from 0-500 mm along the axis 70, and the subject 12 is a wrist of a patient, the interface 66 may show an initial range between the bottom 72 and top 74 of the image stack 30 as being 0-60 mm, with the axis 70 being shown as having a range of 0-100 mm. If the operator adjust the second marker 26 to be outside 60 mm, e.g., 70 mm, then the interface 66 may be refreshed to show the axis 70 as having a range from 0-130 mm.

As further illustrated in FIGS. 8 and 9, in embodiments, the interface 66 may include a reference image 76 that depicts at least one of an orientation and a size of the image stack 30. In other words, the reference image 76 may include sufficient details/graphics and/or other information to convey, to an operator of the system 10, the location and/or orientation of the image stack 30, and/or the location and/or orientation of the images 32, 34, 36, 38, 40 within the stack 30, with respect to the subject 12 and/or the system 10. As will be appreciated, the reference image 76 may be at least one of: an optical image of the subject 12, e.g., a digital picture of the subject 12; a depth image of the subject 12, e.g., a light imaging, detection, and ranging ("LIDAR"); a scout image/pre-shot of the subject 12 acquired via the radiation source 14 and detector 16; and/or any other suitable image/graphic.

Figure 10:
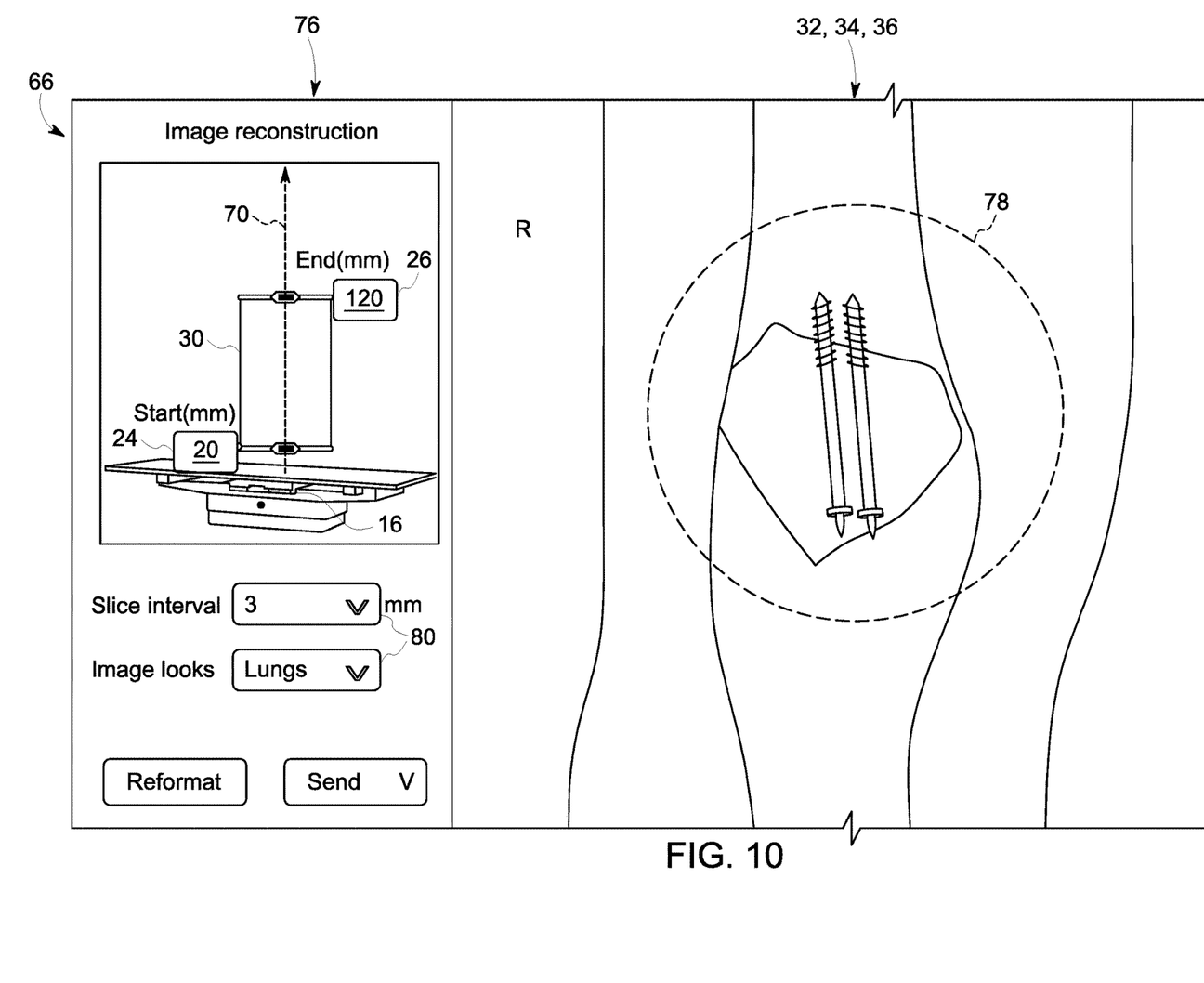
FIG. 10 is yet another graphical display of the interface of the system of FIG. 1, in accordance with an embodiment if the invention.
Figure 11:
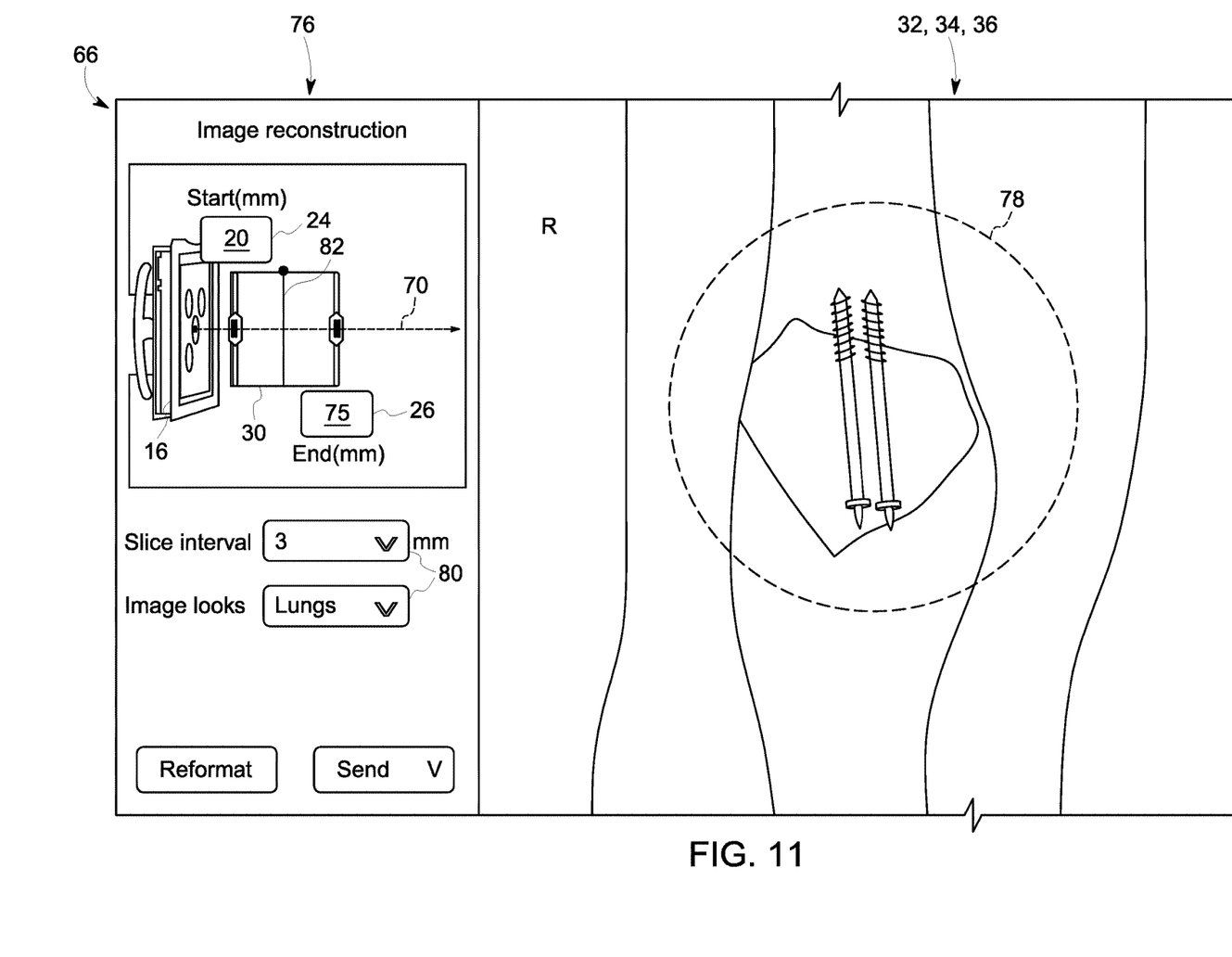
FIG. 11 is still yet another graphical display of the interface of the system of FIG. 1, in accordance with an embodiment if the invention.

Turning to FIGS. 10 and 11, in embodiments, the interface 66 may display one or more of the images 32, 34, 36 reconstructed on demand, which may be in conjunction with the reference image 76. As will be appreciated, display of the on demand reconstructed images 32, 34, 36 provides the operator of the system 10 an opportunity to verify and/or adjust one or more parameters of the system 10 prior to committing to reconstruction of the entire image stack 30.

For example, in an embodiment, an operator may position the subject 12 on the support structure/table 54 (FIG. 1), and the system 10 may then display two markers 24 and 26 on the interface 66 along with a first image 32 reconstructed on demand from the bottom 72 of the image stack 30, e.g., the slice of the stack 30 closest to the subject 12 along the axis 70. Accordingly, the operator can view the image 32 to ensure that the image 32 at the bottom 72 of the stack 30 is acceptable, e.g., includes/covers an area of interest 78 within the volume 68. In the event that the image 32 is unacceptable to the operator, e.g., fails to include the area of interest 78, the operator may move/adjust a first marker 24, which in turn moves the bottom 72 of the image stack 30 to the location along the axis 70 corresponding to the marker 24. In response, the controller 18 may then again reconstruct and re-display the image 32 corresponding to the bottom 72 of the image stack 30. The aforementioned process may be repeated as necessary until the slice/image 32 at the bottom 72 of the image stack 30 is acceptable to the operator.

The controller 18 may then display a second image 34 reconstructed on demand from the top 74 of the image stack 30, e.g., the slice 34 of the stack 30 farthest from the subject 12 along the axis 70. Accordingly, the operator can view the image 34 to ensure that the image 34 at the top 74 of the stack 30 is acceptable, e.g., includes/covers an area of interest 78 within the volume 68. In the event that the image 34 is unacceptable to the operator, e.g., the image 34 fails to include the area of interest 78, the operator may move/adjust the second marker 26, which in turn moves the top 74 of the image stack 30 to the location along the axis 70 corresponding to the marker 26. In response, the controller 18 may then again reconstruct and re-display the image 34 corresponding to the top 74 of the image stack 30. The aforementioned process may be repeated as necessary until the slice/image 34 at the top 74 of the image stack 30 is acceptable to the operator. As will be appreciated, a similar process may be completed with a slice, e.g., slice 36 (FIG. 7), disposed between the top 74 and the bottom 72 of the image stack 30.

As also shown in FIGS. 10 and 11, in embodiments, the interface 66 may include an adjuster 80, e.g., a user input and/or control such as a slide bar, text box, radio button, etc., that provides for the controller 18 to receive and/or adjust a reconstruction parameter, which, in embodiments, may include at least one of: a sampling factor; a slice interval, i.e., the spacing between slices within the image stack 30; an image look, and any combination thereof. Upon receiving a reconstruction parameter, and/or an adjustment thereof, the controller 18 may proceed to reconstruct the images 32, 34, 36 on demand for display in the interface 66 as described above. Thus, similar to confirming the range, e.g., bottom 72 and top 74 positions, of the imaging stack 30 via the markers 24, 26 as discussed above, an operator of the system 10 may view the on demand reconstructed images 32, 34, 36 to confirm whether the reconstruction parameters are acceptable, and if not, adjust them accordingly prior to committing the entire imaging stack 30 to reconstruction.

In embodiments, the interface 66 may also include an image selector 82 (FIGS. 9 and 11), which, in embodiments, may provide for a user to select a particular image 32, 34, 36 within the image stack 30 for reconstruction. For example, the image selector 82 may a be marker/slide bar that slides along the axis 70 within the interface 66 such that the image 34 shown within the interface 34 corresponds to the location of the image selector 82 along the axis 70.

Finally, it is also to be understood that the imaging system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein, which may be accomplished in real-time. For example, as previously mentioned, the system may include at least one processor and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium," as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for imaging a subject is provided. The system includes a radiation source, a radiation detector, and a controller. The radiation source is operative to transmit electromagnetic rays through the subject. The radiation detector is operative to receive the electromagnetic rays after having passed through the subject so as to generate a plurality of projections of the subject. The controller is operative to display one or more selectively adjustable markers that define an image stack. The controller is further operative to reconstruct one or more images within the image stack based at least in part on the plurality of projections. Reconstruction of the one or more images is on demand. In certain embodiments, the controller is further operative to display a reference image that depicts at least one of an orientation and a size of the image stack. In certain embodiments, the reference image is at least one of an optical image of the subject, a depth image of the subject; a scout image of the subject, and an image of the system. In certain embodiments, the controller reconstructs the one or more images on demand after at least one of the one or more selectively adjustable markers has been selectively adjusted. In certain embodiments, a first marker of the one or more selectively adjustable markers corresponds to a first end of the image stack, and a second marker of the one or more selectively adjustable markers corresponds to a second end of the image stack opposite the first end. In certain embodiments, the controller is further operative to display an adjustor that provides for the controller to receive a reconstruction parameter. In such embodiments, on demand reconstruction of the one or more images is further based at least in part the received reconstruction parameter. In certain embodiments, the reconstruction parameter is at least one of a sampling factor, a slice interval, and an image look. In certain embodiments, the electromagnetic rays are x-rays.

Other embodiments provide for a method for imaging a subject. The method includes displaying, via a controller, one or more selectively adjustable markers that define an image stack; and reconstructing, via the controller, one or more images within the image stack based at least in part on a plurality of projections generated by receiving, at a radiation detector, electromagnetic rays transmitted through the subject via a radiation source. Reconstruction of the one or more images is on demand. In certain embodiments, the method further includes displaying a reference image that depicts at least one of an orientation and a size of the image stack. In certain embodiments, the reference image is at least one of an optical image of the subject, a depth image of the subject; a scout image of the subject, and an image of a system that includes the radiation source and the radiation detector. In certain embodiments, the method further includes selectively adjusting the one or more selectively adjustable markers. In such embodiments, reconstructing, via a controller, one or more images within the image stack occurs after the one or more selectively adjustable markers has been selectively adjusted. In certain embodiments, a first marker of the one or more selectively adjustable markers corresponds to a first end of the image stack, and a second marker of the one or more selectively adjustable markers corresponds to a second end of the image stack opposite the first end. In certain embodiments, the method further includes displaying an adjustor that provides for the controller to receive a reconstruction parameter. In such embodiments, on demand reconstruction of the one or more images is further based at least in part the received reconstruction parameter. In certain embodiments, the reconstruction parameter is at least one of a sampling factor, a slice interval, and an image look. In certain embodiments, the electromagnetic rays are x-rays.

Yet still other embodiments provide for a non-transitory computer readable medium storing instructions. The stored instructions are configured to adapt a controller to display one or more selectively adjustable markers that define an image stack. The stored instructions are further configured to adapt the controller to reconstruct one or more images within the image stack based at least in part on a plurality of projections generated by receiving, at a radiation detector, electromagnetic rays transmitted through a subject via a radiation source. Reconstruction of the one or more images is on demand. In certain embodiments, the stored instructions are further configured to adapt the controller to display a reference image that depicts at least one of an orientation and a size of the image stack. In certain embodiments, the reference image is at least one of an optical image of the subject, a depth image of the subject, a scout image of the subject, and an image of a system that includes the radiation source and the radiation detector. In certain embodiments, the stored instructions are further configured to adapt the controller to display an adjustor that provides for the controller to receive a reconstruction parameter. In such embodiments, on demand reconstruction of the one or more images is further based at least in part the received reconstruction parameter.

Accordingly, as will be appreciated, by providing for on demand reconstruction of one or more images, as discussed above, some embodiments of the present invention provide for operators to adjust one or more reconstruction parameters prior to committing to reconstruction of an entire image stack. Thus, some embodiments of the present invention reduce the time of a scanning procedure over traditional imaging systems, in which the operator needs to first reconstruct the entire image stack in order to see the results of the selected reconstruction parameters.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for imaging a subject comprising:
a radiation source operative to transmit electromagnetic rays through the subject;
a radiation detector configured to receive the electromagnetic rays after passing through the subject so as to generate a plurality of projections of the subject; and,
a controller operative to:
display one or more selectively adjustable markers that define an image stack;
reconstruct one or more images on demand within the image stack based at least in part on the plurality of projections; and
wherein the one or more on demand images are separately reconstructed by the controller prior to reconstruction of a majority of images in the image stack.

2. The system of claim 1, wherein the controller is further operative to:
display a reference image that depicts at least one of an orientation and a size of the image stack.

3. The system of claim 2, wherein the reference image is at least one of an optical image of the subject, a depth image of the subject; a scout image of the subject, and an image of the system.

4. The system of claim 1, wherein the controller reconstructs the one or more images on demand after at least one of the one or more selectively adjustable markers has been selectively adjusted.

5. The system of claim 1, wherein a first marker of the one or more selectively adjustable markers corresponds to a first end of the image stack and a second marker of the one or more selectively adjustable markers corresponds to a second end of the image stack opposite the first end.

6. The system of claim 1, wherein the controller is further operative to:
display an adjustor that provides for the controller to receive a reconstruction parameter, and
wherein on demand reconstruction of the one or more images is further based at least in part the received reconstruction parameter.

7. The system of claim 6, wherein the reconstruction parameter is at least one of a sampling factor, a slice interval, and an image look.

8. The system of claim 1, wherein the electromagnetic rays are x-rays.

9. A method for imaging a subject comprising:
displaying, via a controller, one or more selectively adjustable markers that define an image stack;
reconstructing on demand, via the controller, one or more images within the image stack based at least in part on a plurality of projections generated by receiving, at a radiation detector, electromagnetic rays transmitted through the subject via a radiation source; and
wherein the one or more on demand images are separately reconstructed by the controller prior to reconstruction of a majority of images in the image stack.

10. The method of claim 9 further comprising:
displaying a reference image that depicts at least one of an orientation and a size of the image stack.

11. The method of claim 10, wherein the reference image is at least one of an optical image of the subject, a depth image of the subject; a scout image of the subject, and an image of a system that includes the radiation source and the radiation detector.

12. The method of claim 9 further comprising:
selectively adjusting the one or more selectively adjustable markers; and
wherein reconstructing, via a controller, one or more images within the image stack occurs after the one or more selectively adjustable markers has been selectively adjusted.

13. The method of claim 9, wherein a first marker of the one or more selectively adjustable markers corresponds to a first end of the image stack and a second marker of the one or more selectively adjustable markers corresponds to a second end of the image stack opposite the first end.

14. The method of claim 9 further comprising:
displaying an adjustor that provides for the controller to receive a reconstruction parameter; and
wherein on demand reconstruction of the one or more images is further based at least in part the received reconstruction parameter.

15. The method of claim 14, wherein the reconstruction parameter is at least one of a sampling factor, a slice interval, and an image look.

16. The method of claim 9, wherein the electromagnetic rays are x-rays.

17. A non-transitory computer readable medium storing instructions configured to adapt a controller to:
display one or more selectively adjustable markers that define an image stack;
reconstruct on demand one or more images within the image stack based at least in part on a plurality of projections generated by receiving, at a radiation detector, electromagnetic rays transmitted through a subject via a radiation source; and
wherein the one or more on demand images are separately reconstructed by the controller prior to reconstruction of a majority of images in the image stack.

18. The non-transitory computer readable medium of claim 17, wherein the stored instructions are further configured to adapt the controller to:
display a reference image that depicts at least one of an orientation and a size of the image stack.

19. The non-transitory computer readable medium of claim 18, wherein the reference image is at least one of an optical image of the subject, a depth image of the subject, a scout image of the subject, and an image of a system that includes the radiation source and the radiation detector.

20. The non-transitory computer readable medium of claim 17, wherein the stored instructions are further configured to adapt the controller to:
display an adjustor that provides for the controller to receive a reconstruction parameter; and
wherein on demand reconstruction of the one or more images is further based at least in part the received reconstruction parameter.

* * * * *